United States Patent
Shelton, IV et al.

(10) Patent No.: US 8,257,251 B2
(45) Date of Patent: Sep. 4, 2012

(54) METHODS AND DEVICES FOR PROVIDING ACCESS INTO A BODY CAVITY

(75) Inventors: Frederick E. Shelton, IV, Hillsboro, OH (US); Christopher W. Widenhouse, Clarksville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 565 days.

(21) Appl. No.: 12/420,146

(22) Filed: Apr. 8, 2009

(65) Prior Publication Data

US 2010/0261974 A1  Oct. 14, 2010

(51) Int. Cl.
*A61B 1/32* (2006.01)

(52) U.S. Cl. ....................................................... 600/206

(58) Field of Classification Search .................. 600/201, 600/205, 206, 208, 210, 215, 227, 231, 235
See application file for complete search history.

(56) References Cited

U.S. PATENT DOCUMENTS

| | | |
|---|---|---|
| 1,982,784 A | 12/1934 | Buckley |
| 2,129,391 A | 9/1938 | Wappler |
| 3,402,710 A | 9/1968 | Paleschuck |
| 3,654,965 A | 4/1972 | Gramain |
| 3,799,152 A | 3/1974 | Kim |
| 4,112,932 A | 9/1978 | Chiulli |
| 4,306,545 A | 12/1981 | Ivan et al. |
| 4,379,458 A | 4/1983 | Bauer et al. |
| 4,402,683 A | 9/1983 | Kopman |
| 4,417,888 A | 11/1983 | Cosentino et al. |
| 4,466,523 A * | 8/1984 | De Carolis et al. .......... 192/43.1 |
| 5,010,925 A | 4/1991 | Atkinson et al. |
| 5,091,435 A | 2/1992 | Suzuki et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |
| 5,269,772 A | 12/1993 | Wilk |
| 5,308,336 A | 5/1994 | Hart et al. |
| 5,312,417 A | 5/1994 | Wilk |
| 5,320,611 A | 6/1994 | Bonutti et al. |
| 5,342,315 A | 8/1994 | Rowe et al. |

(Continued)

FOREIGN PATENT DOCUMENTS

DE    19814576 A1    10/1999

(Continued)

OTHER PUBLICATIONS

European Search Report dated Aug. 11, 2010 for EP App. No. 10250734.0 (7 pages).

(Continued)

*Primary Examiner* — Cris L Rodriguez
*Assistant Examiner* — Eric Rosen
(74) *Attorney, Agent, or Firm* — Nutter McClennen & Fish LLP

(57) ABSTRACT

Methods and devices are provided for providing surgical access into a body cavity. In one embodiment, a surgical access device is provided that includes a proximal housing and a distal retractor. At least one stability thread can extend around a perimeter of at least a portion of the distal retractor. In some embodiments, the stability thread can be mechanically adjustable to change a diameter of the distal retractor.

18 Claims, 9 Drawing Sheets

U.S. PATENT DOCUMENTS

| | | |
|---|---|---|
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,514,133 A | 5/1996 | Golub et al. |
| 5,524,644 A | 6/1996 | Crook |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,640,977 A | 6/1997 | Leahy et al. |
| 5,643,301 A | 7/1997 | Mollenauer |
| 5,649,550 A | 7/1997 | Crook |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,795,289 A | 8/1998 | Wyttenbach |
| 5,797,888 A | 8/1998 | Yoon |
| 5,803,919 A | 9/1998 | Hart et al. |
| 5,813,409 A | 9/1998 | Leahy et al. |
| 5,814,058 A | 9/1998 | Carlson et al. |
| 5,827,319 A | 10/1998 | Carlson et al. |
| 5,843,040 A | 12/1998 | Exline |
| 5,853,395 A | 12/1998 | Crook et al. |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,990,382 A | 11/1999 | Fox |
| 5,997,515 A | 12/1999 | de la Torre et al. |
| 6,024,736 A | 2/2000 | de la Torre et al. |
| 6,033,426 A | 3/2000 | Kaji |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,254,534 B1 | 7/2001 | Butler et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,450,983 B1 | 9/2002 | Rambo |
| 6,454,783 B1 | 9/2002 | Piskun |
| 6,458,077 B1 | 10/2002 | Boebel et al. |
| 6,488,620 B1 | 12/2002 | Segermark et al. |
| 6,497,724 B1 | 12/2002 | Stevens et al. |
| 6,551,270 B1 | 4/2003 | Bimbo et al. |
| 6,551,282 B1 | 4/2003 | Exline et al. |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,846,287 B2 | 1/2005 | Bonadio et al. |
| 6,887,194 B2 | 5/2005 | Hart et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 2002/0068923 A1 | 6/2002 | Caldwell et al. |
| 2002/0097793 A1 | 7/2002 | Struhsaker et al. |
| 2002/0156432 A1 | 10/2002 | Racenet et al. |
| 2002/0183594 A1 | 12/2002 | Beane et al. |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0049099 A1 | 3/2004 | Ewers et al. |
| 2004/0082969 A1 | 4/2004 | Kerr |
| 2004/0097793 A1 | 5/2004 | Butler et al. |
| 2004/0106942 A1 | 6/2004 | Taylor et al. |
| 2004/0117032 A1 | 6/2004 | Roth |
| 2004/0127772 A1 | 7/2004 | Ewers et al. |
| 2004/0138528 A1 | 7/2004 | Richter et al. |
| 2004/0154624 A1 | 8/2004 | Bonadio et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2004/0267096 A1 | 12/2004 | Caldwell et al. |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0119722 A1 | 6/2005 | Styrc et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |

| | | |
|---|---|---|
| 2006/0030755 A1 | 2/2006 | Ewers et al. |
| 2006/0058575 A1* | 3/2006 | Zaddem et al. ............ 600/30 |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1* | 11/2006 | Bonadio et al. ............ 600/208 |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088204 A1 | 4/2007 | Albrecht et al. |
| 2007/0088258 A1 | 4/2007 | Wenchell et al. |
| 2007/0088277 A1 | 4/2007 | McGinley et al. |
| 2007/0118021 A1 | 5/2007 | Pokorney |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0208312 A1 | 9/2007 | Norton et al. |
| 2007/0255219 A1 | 11/2007 | Vaugh et al. |
| 2007/0270654 A1 | 11/2007 | Pignato et al. |
| 2008/0009797 A1 | 1/2008 | Stellon et al. |
| 2008/0025519 A1 | 1/2008 | Yu et al. |
| 2008/0027476 A1 | 1/2008 | Piskun |
| 2008/0051739 A1 | 2/2008 | McFarlane |
| 2008/0058728 A1 | 3/2008 | Soltz et al. |
| 2008/0065021 A1 | 3/2008 | Jenkins et al. |
| 2008/0086080 A1 | 4/2008 | Mastri et al. |
| 2008/0119821 A1 | 5/2008 | Agnihotri et al. |
| 2008/0132765 A1 | 6/2008 | Beckman et al. |
| 2008/0255519 A1 | 10/2008 | Piskun et al. |
| 2008/0281161 A1 | 11/2008 | Albrecht et al. |
| 2009/0005799 A1 | 1/2009 | Franer et al. |
| 2009/0082731 A1 | 3/2009 | Moreno |
| 2009/0118587 A1 | 5/2009 | Voegele et al. |
| 2009/0187079 A1 | 7/2009 | Albrecht et al. |
| 2009/0270685 A1 | 10/2009 | Moreno et al. |
| 2009/0270686 A1 | 10/2009 | Duke et al. |
| 2009/0270818 A1 | 10/2009 | Duke |
| 2010/0010310 A1 | 1/2010 | Weisenburgh, II et al. |
| 2010/0030260 A1 | 2/2010 | Fleischmann |
| 2010/0081863 A1 | 4/2010 | Hess et al. |
| 2010/0081864 A1 | 4/2010 | Hess et al. |
| 2010/0081871 A1 | 4/2010 | Widenhouse et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0113883 A1 | 5/2010 | Widenhouse et al. |
| 2010/0139051 A1* | 6/2010 | Bourke et al. ............ 24/115 R |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0249525 A1 | 9/2010 | Shelton, IV et al. |
| 2010/0261970 A1 | 10/2010 | Shelton, IV et al. |
| 2010/0261972 A1 | 10/2010 | Widenhouse et al. |
| 2010/0261974 A1 | 10/2010 | Shelton, IV et al. |
| 2010/0262080 A1 | 10/2010 | Shelton, IV et al. |
| 2010/0268162 A1 | 10/2010 | Shelton, IV et al. |
| 2010/0274093 A1 | 10/2010 | Shelton, IV |
| 2010/0280327 A1 | 11/2010 | Nobis et al. |
| 2010/0312060 A1 | 12/2010 | Widenhouse et al. |
| 2010/0312061 A1 | 12/2010 | Hess et al. |
| 2010/0312062 A1 | 12/2010 | Cropper et al. |
| 2010/0312063 A1 | 12/2010 | Hess et al. |
| 2010/0312064 A1 | 12/2010 | Weisenburgh, II et al. |
| 2010/0312065 A1 | 12/2010 | Shelton, IV et al. |
| 2010/0312066 A1 | 12/2010 | Cropper et al. |
| 2010/0312189 A1 | 12/2010 | Shelton, IV et al. |

FOREIGN PATENT DOCUMENTS

| | | |
|---|---|---|
| DE | 20022005 U1 | 4/2001 |
| DE | 102007011570 A1 | 9/2008 |
| EP | 0568383 | 11/1993 |
| EP | 568383 A1 | 11/1993 |
| EP | 577400 A1 | 1/1994 |
| EP | 0637431 A1 | 2/1995 |
| EP | 0646358 | 4/1995 |
| EP | 646358 A1 | 4/1995 |
| EP | 709918 | 5/1996 |
| EP | 0776231 A1 | 6/1997 |
| EP | 0776231 B1 | 6/1997 |
| EP | 950376 | 10/1999 |
| EP | 1135070 | 9/2001 |
| EP | 1219251 A1 | 7/2002 |
| EP | 1219251 A1 | 7/2002 |
| EP | 1219252 A1 | 7/2002 |
| EP | 1219252 A1 | 7/2002 |
| EP | 1219253 A1 | 7/2002 |
| EP | 1219253 A1 | 7/2002 |
| EP | 1312318 A1 | 5/2003 |
| EP | 1350476 | 10/2003 |
| EP | 1702575 A2 | 9/2006 |
| EP | 1731105 A1 | 12/2006 |
| EP | 1731105 A1 | 12/2006 |
| EP | 1774918 A1 | 4/2007 |
| EP | 2119404 A1 | 11/2009 |
| EP | 2181657 A2 | 5/2010 |
| FR | 2710270 | 3/1995 |
| FR | 2710270 A1 | 3/1995 |
| JP | 2006320750 | 11/2006 |
| WO | 9407552 | 4/1994 |
| WO | 9407552 A1 | 4/1994 |
| WO | WO-95/24864 A1 | 9/1995 |
| WO | 9602297 A1 | 2/1996 |
| WO | 9608897 A1 | 3/1996 |
| WO | 9636283 A1 | 11/1996 |
| WO | 9743958 A1 | 11/1997 |
| WO | WO-9848724 A1 | 11/1998 |
| WO | 0032263 A1 | 6/2000 |
| WO | WO-0032116 A1 | 6/2000 |
| WO | 0041759 A1 | 7/2000 |
| WO | WO-00/54676 A1 | 9/2000 |
| WO | WO-00/54677 A1 | 9/2000 |
| WO | 0108563 A2 | 2/2001 |
| WO | WO-0126558 A1 | 4/2001 |
| WO | 0217800 A2 | 3/2002 |
| WO | WO-02/34108 A2 | 5/2002 |
| WO | 2004030515 A2 | 4/2004 |
| WO | WO-2004/030547 A1 | 4/2004 |
| WO | WO-2004/054456 A1 | 7/2004 |
| WO | WO-2004/096012 A2 | 11/2004 |
| WO | 2005000454 A1 | 1/2005 |
| WO | 2005087112 A1 | 9/2005 |
| WO | WO-2005087112 A1 | 9/2005 |
| WO | 2005094432 A2 | 10/2005 |
| WO | 2005097019 A2 | 10/2005 |
| WO | 2005097234 A2 | 10/2005 |
| WO | WO-2005094432 A2 | 10/2005 |
| WO | 2006057982 A2 | 6/2006 |
| WO | 2007008741 A1 | 1/2007 |
| WO | 2007119232 A2 | 10/2007 |
| WO | WO-2007119232 A2 | 10/2007 |
| WO | 2008024502 A2 | 2/2008 |
| WO | WO-2008024502 A2 | 2/2008 |
| WO | 2008028149 A2 | 3/2008 |
| WO | 2008121294 A1 | 10/2008 |
| WO | 2009035663 A2 | 3/2009 |

OTHER PUBLICATIONS

International Search Report and Written Opinion for International App. No. PCT/US2010/036811 dated Sep. 14, 2010 (6 pages).

International Search Report, from PCT/US10/36829, mailed Sep. 9, 2010 (5 pages).

European Search Report, EP 10250732, dated Jul. 28, 2010.

International Search Report and Written Opinion for Application No. PCT/US2010/037190, dated Sep. 22, 2010 (15 pages).

"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport >R-Port laparoscopic access device > Advanced Surgical Concepts ACS" Ideas For Surgery.com, Dec. 2007, 4 pages.

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp. 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

International Search Report and Written Opinion for Application No. PCT/US2010/036806, dated Sep. 3, 2010 (8 pages).

International Search Report and Written Opinion for Application No. PCT/US2010/036820, dated Oct. 22, 2010 (18 pages).

U.S. Appl. No. 12/242,333, filed Sep. 30, 2008.
U.S. Appl. No. 12/242,353, filed Sep. 30, 2008.
U.S. Appl. No. 12/242,381, filed Sep. 30, 2008.
U.S. Appl. No. 12/242,711, filed Sep. 30, 2008.
U.S. Appl. No. 12/242,721, filed Sep. 30, 2008.
U.S. Appl. No. 12/242,726, filed Sep. 30, 2008.
U.S. Appl. No. 12/242,765, filed Sep. 30, 2008.
U.S. Appl. No. 12/399,482, filed Mar. 6, 2009.
U.S. Appl. No. 12/399,547, filed Mar. 6, 2009.
U.S. Appl. No. 12/399,625, filed Mar. 6, 2009.
U.S. Appl. No. 12/420,107, filed Apr. 8, 2009.
U.S. Appl. No. 12/420,202, filed Apr. 8, 2009.
U.S. Appl. No. 12/420,232, filed Apr. 8, 2009.

* cited by examiner

METHODS AND DEVICES FOR PROVIDING ACCESS INTO A BODY CAVITY

FIELD OF THE INVENTION

The present invention relates to methods and devices for providing surgical access into a body cavity.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become more common as they provide minimally invasive techniques for establishing a portal for a number of procedures, such as those involving the abdominal cavity. Reduced postoperative recovery time, markedly decreased post-operative pain and wound infection, and improved cosmetic outcome are well established benefits of minimally invasive surgery, derived mainly from the ability of surgeons to perform an operation utilizing smaller incisions of the body cavity wall.

In many surgical procedures, it is desirable to provide one or more working channels into a body cavity through which various instruments can be passed to view, engage, and/or treat tissue to achieve a diagnostic or therapeutic effect. In laparoscopic abdominal procedures for example, the abdominal cavity is generally insufflated with $CO_2$ gas to a pressure of around 15 mm Hg. The abdominal wall is pierced and one or more tubular cannulas, each defining a working channel, are inserted into the abdominal cavity. A laparoscopic telescope connected to an operating room monitor can be used to visualize the operative field and can be placed through one of the working channels. Other laparoscopic instruments such as graspers, dissectors, scissors, retractors, etc. can also be placed through one or more of the working channels to facilitate various manipulations by the surgeon and/or surgical assistant(s).

One problem with existing methods and devices is that existing surgical access devices do not retract tissue beyond the initial incision to any appreciable degree. It can thus be difficult to position a surgical access device in the incision, particularly in minimally invasive surgical procedures where the incision is relatively small. It can also be difficult as an initial matter to choose an appropriately sized access device to position within the incision during the stress and time constraints of surgery.

It can also be difficult to remove an access device from an incision in tissue when the access device is snugly positioned therein, requiring an amount of pullout force that can cause damage to the tissue and/or prolong length of the surgical procedure. Such forceful removal of the access device can also increase the size of the incision, thereby reducing the healing and cosmetic benefits of a minimally invasive surgical procedure.

Accordingly, there remains a need for methods and devices for providing surgical access into a body cavity.

SUMMARY OF THE INVENTION

The present invention generally provides methods and devices for providing surgical access into a body cavity. In one embodiment, a surgical access device is provided that includes a proximal external portion, a distal portion including a flexible retractor configured to be positioned in tissue of a body to form a pathway therethrough into a body cavity, and an actuation member, e.g., a stability thread or actuation cable, spiraling around a perimeter of the retractor. The actuation member is configured to selectively effect a change in a diameter of the retractor.

In some embodiments, the device can include an actuator configured to change a tension of the actuation member to selectively effect the change in the diameter of the retractor. The actuator can have a variety of configurations, such as a ratchet mechanism. The ratchet mechanism can include a pawl configured to engage at least one of a plurality of teeth and to be movable to selectively effect the change in the diameter of the retractor. The pawl can be configured to be freely slidably movable in a first direction to selectively effect the change in the diameter of the retractor and to be prevented from moving in a second, opposite direction. The pawl can be configured to move radially inward relative to the retractor to disengage the pawl from engagement with the at least one of a plurality of teeth to allow the pawl to move in the first direction or the second direction to engage at least one other of the plurality of the teeth.

The device can vary in any other number of ways. For example, a first terminal end of the actuation member can be attached to a distal end of the retractor and a second terminal end of the actuation member extends through the proximal external portion. For another example, selectively effecting the change in the diameter of the retractor can not substantially change a longitudinal length of the retractor. For yet another example, the retractor can have a lumen extending through a sidewall thereof, and the actuation member can be disposed in the lumen. For still another example, the retractor in a default state can have a first diameter, and actuating the actuation member with the retractor in the default state can move the retractor to a second state in which the retractor has a second diameter that is less than or greater than the first diameter.

In another aspect, a method of providing access through tissue to a body cavity is provided that includes positioning a retractor in an opening in tissue such that a working channel of the retractor provides access through the tissue and into a body cavity, and moving an actuation member extending around a perimeter of the working channel to change a length of the actuation member extending around the perimeter of the working channel and to change a size of a diameter of the retractor. In some embodiments, the method can include locking the actuation member in a fixed position relative to the retractor to maintain the size of the opening in tissue. The method can vary in any other number of ways. For example, changing the length of the actuation member extending around the perimeter of the working channel can include selectively increasing or decreasing the length of the actuation member extending around the perimeter of the working channel. For another example, moving the actuation member extending around the perimeter of the working channel can include moving a pawl coupled to the actuation member in a radial direction relative to the retractor.

In another embodiment, a method of providing access through tissue to a body cavity includes positioning a flexible retractor having a cross-sectional shape in the form of an ellipse in an opening in tissue such that the retractor forms a pathway through the tissue and into a body cavity and such that a major axis of the ellipse is substantially parallel to a major axis of the opening in tissue, and positioning the major axis of the ellipse substantially perpendicular to the major axis of the opening in tissue to expand the opening in tissue. The method can have any number of variations. For example, expanding the opening in tissue can include moving the opening in tissue from a linear shape to a substantially circular shape. For another example, positioning the major axis of the ellipse substantially perpendicular to the major axis of the opening in tissue can cause the flexible retractor to change from having the cross-sectional shape in the form of an ellipse to having a cross-sectional shape in the form of a circle. For still another example, positioning the flexible retractor in the opening in tissue can include aligning at least one of a plurality of rings disposed around a perimeter of the retractor within the opening in tissue. Positioning the major axis of the ellipse substantially perpendicular to the major axis of the opening in tissue can cause the at least one of the plurality of rings to move from an elliptical shape to a circular shape. Each of the plurality of rings can have an elliptical shape at least when the retractor is in a first state and not subjected to a compressive force.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
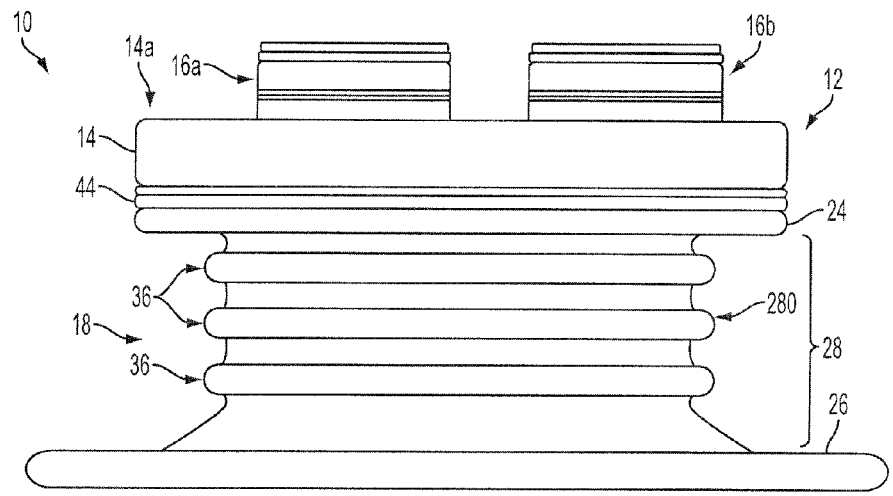
FIG. 1 is a side view of one embodiment of a surgical access device having a plurality of rings disposed around a retractor of the device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for providing surgical access into a body cavity. In general, the methods and devices allow a surgical access device to be securely positioned within an opening in tissue to provide access to a body cavity underlying the tissue. In one embodiment, a surgical access device can include a proximal housing and a distal retractor. At least one stability thread can extend around a perimeter of at least a portion of the distal retractor to provide structural integrity to the distal retractor and help secure the device within an opening formed in the tissue. In some embodiments, the stability thread can be mechanically adjustable to change a diameter of the distal retractor, thereby allowing the device to adapt to different sized openings in tissue and to be more easily positioned therein and removed therefrom. The surgical access device can provide active retraction of the opening formed in tissue to help securely position the device within the tissue. Such secure positioning can help form a better seal between the tissue and the device and help retain the tissue in a more stable position when the device is positioned therein. The device can also dilate the tissue when positioned therein to help improve the seal integrity between the device and the tissue. Such dilation of the tissue by the device can increase a size and/or change the shape of the opening in the tissue to increase working space available through the tissue opening. Having more working space through the tissue can help reduce interference between multiple surgical instruments inserted therethrough and/or allow larger and/or a greater number of surgical instruments to be inserted therethrough.

The various surgical access devices described herein can generally be configured to allow one or more surgical instruments to be inserted therethrough through one or more independent sealing ports or access ports formed in a proximal housing, hereinafter generally referred to as a housing, of the device and into a body cavity. The sealing ports can each define working channels extending through the proximal housing and aligned with a distal retractor. The distal retractor, hereinafter generally referred to as a retractor, can be configured as a wound protector, or other member for forming a pathway through tissue. The retractor can extend from the proximal housing of the device, and it can be configured to be positioned within an opening in a patient's body, such as the umbilicus. Any and all of the surgical access devices described herein can also include various other features, such as one or more ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

Any and all embodiments of a surgical access device can also include one or more safety shields positioned through, in, and around any of the components and/or tissue to protect the components against puncture or tear by surgical instruments being inserted through the device. Exemplary embodiments of safety shields are described in more detail in U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, which are hereby incorporated by reference in their entireties.

In any and all of the surgical access device embodiments disclosed herein, an engagement and/or release mechanism can be included to allow certain components of the surgical access device to be removable as needed. Any engagement and release mechanism known in the art, e.g., a snap-lock mechanism, corresponding threads, etc., can be used to releasably mate components of the device. Exemplary embodiments of an engagement and release mechanisms are described in more detail in previously mentioned U.S. patent application Ser. No. 12/242,765 entitled "Surgical Access Device" filed on Sep. 30, 2008, U.S. patent application Ser. No. 12/399,625 entitled "Methods and Devices for Providing Access to a Body Cavity" filed on Mar. 6, 2009, and U.S. patent application Ser. No. 12/399,482 entitled "Methods and Devices for Providing Access to a Body Cavity" filed on Mar. 6, 2009 and in U.S. Pat. No. 7,371,227 entitled "Trocar Seal Assembly," issued May 13, 2008 and U.S. Pat. No. 5,628,732 entitled "Trocar With Improved Universal Seal," issued May 13, 2007, which are hereby incorporated by reference in their entireties.

In use, as further discussed below, the surgical access devices disclosed herein can be used to provide access to a patient's body cavity. The device's retractor is positionable within an opening in a patient's body such that a distal portion of the retractor extends into a patient's body cavity and a proximal portion configured to couple to the device's housing is positioned adjacent to the patient's skin on an exterior of the patient's body. A lumen in the retractor can form a pathway through the opening in a patient's body so that surgical instruments can be inserted from outside the body to an interior body cavity. The elasticity of the skin of the patient can assist in the retention of the retractor in the body opening or incision made in the body. The retractor can be placed in any opening within a patient's body, whether a natural orifice or an opening made by an incision. As a non-limiting example, the retractor can be placed through the umbilicus. In one embodiment, the retractor can be substantially flexible so that it can easily be maneuvered into and within tissue as needed. In other embodiments, the retractor can be substantially rigid or substantially semi-rigid. The retractor can be formed of any suitable material known in the art, e.g., silicone, urethane, thermoplastic elastomer, and rubber.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel created by the sealing port when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment. Exemplary embodiments of various seal protectors are described in more detail in U.S. Pat. No. 5,342,315 entitled "Trocar Seal/Protector Assemblies," issued Aug. 30, 1994 and U.S. Pat. No. 7,163,525 entitled "Duckbill Seal Protector," issued Jan. 16, 2007, which are hereby incorporated by reference in their entireties.

Figure 2:
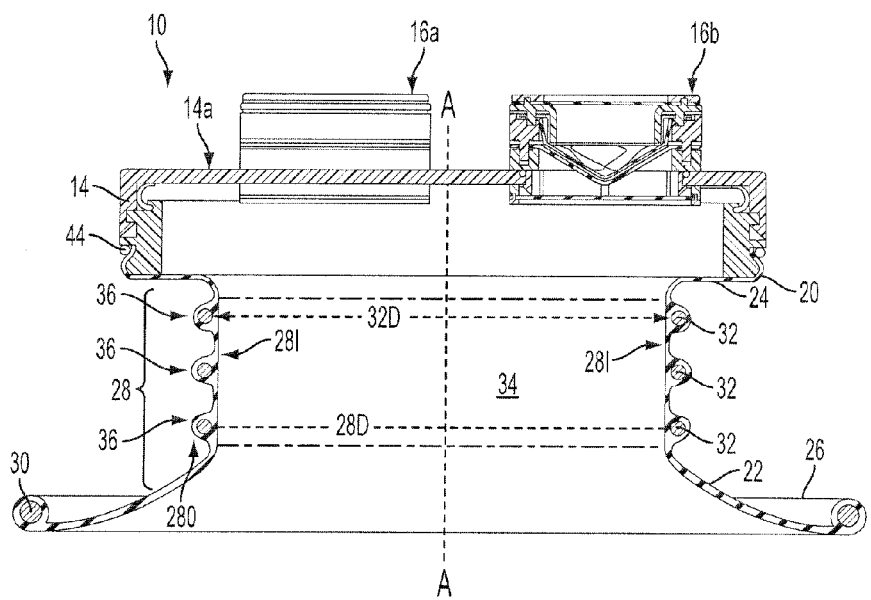
FIG. 2 is a side, cross-sectional view of the device of FIG. 1.

In an exemplary embodiment, shown in FIGS. 1 and 2, a surgical access device 10 is provided having a housing 12 configured to have one or more surgical instruments inserted therethrough. Although the housing 12 can have any configuration, in this illustrated embodiment, the housing 12 includes a seal base 14 that supports at least one sealing or access port and that is configured to form a seat and seal between the base 14 and a distal portion of the device 10, e.g., a retractor 18. The housing 12 can be fixedly or removably coupled to the retractor 18 configured to distally extend from the housing 12 and to provide a pathway through tissue into a body cavity. In this embodiment, the retractor 18 includes a proximal retractor portion or proximal retractor base 20 coupled to a distal retractor portion 22. As shown in this embodiment, the housing 12 can be removably coupled via snap-fit to the retractor 18. The housing 12 can be in a fixed position relative to the retractor 18 as shown in this embodiment, or the housing 12 can be movable relative to the retractor 18. Exemplary embodiments of various housings are described in more detail in previously mentioned U.S. Patent Publication No. 2006/0247673 entitled "Multi-port Laparoscopic Access Device" filed Nov. 2, 2006, U.S. patent application Ser. No. 12/399, 625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, and in U.S. patent application Ser. No. 12/399,547 entitled "Surgical Access Devices And Methods Providing Seal Movement In Predefined Paths" filed on Mar. 6, 2009, which is hereby incorporated by reference in its entirety.

While any number of sealing ports can be formed in the seal base 14, in this illustrated embodiment, first and second sealing ports 16a, 16b extend through the seal base 14. The sealing ports 16a, 16b in this illustrated embodiment each have a central axis that extends substantially perpendicular to a proximal surface 14a of the seal base 14, and the sealing ports 16a, 16b are each in a fixed position relative to the housing 12, but any one or more of the sealing ports can be angled relative to the seal base 14 and/or rotatable or otherwise movable relative to the seal base 14 and/or other portion (s) of the housing 12. Additionally or alternatively, any one or more of the sealing ports 16a, 16b can be configured to be movable relative to any one or more portions of the retractor 18 and/or any others of the sealing ports 16a, 16b. The sealing ports 16a, 16b can be attached or mated to the seal base 14 using any attachment or mating mechanism known in the art, but in the illustrated embodiment the sealing ports 16a, 16b can each mate with the seal base 14 through an interference fit. In general, the sealing ports 16a, 16b can each include a port housing, which can be seated directly or indirectly in a port opening in the seal base 14, and a sealing element, which can be positioned within an associated port housing. A sealing element can include at least one instrument seal and/or at least one channel seal, and can generally be configured to contact an instrument inserted through the sealing element's associated sealing port. Exemplary embodiments of various sealing ports are described in more detail in previously mentioned U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008.

As noted above, the retractor 18 can extend distally from the housing 12, and it can be configured to be positioned in an opening formed in tissue. The retractor 18 can, as shown in this exemplary embodiment, include a substantially flexible distal portion 22 having a proximal flange 24 and a distal flange 26 with an inner elongate portion 28 extending therebetween. A retractor retaining band 44, e.g., an o-ring, can be positioned between the proximal retractor base 20 and the flexible distal portion 22 to help form a secure seal therebetween. The inner elongate portion 28 can have a diameter less than a diameter of the proximal and distal flanges 24, 26, which can have the same diameter or different diameters from one another, and can be configured to be positioned within tissue. The proximal flange 24 can be configured to be seated within the proximal retractor base 20 or, as illustrated in this embodiment, the proximal retractor base 20 can be configured to be seated within the proximal flange 24. The proximal retractor base 20 can optionally be attached to the proximal flange 24 using an adhesive, sealant, complementary threads, or any other attachment mechanism, as will be appreciated by a person skilled in the art. A proximal o-ring (not shown) can optionally be positioned within the proximal flange 24 to help provide structural support to the retractor 18 if the proximal flange 24 is seated within the proximal retractor base 20. A distal o-ring 30 can optionally be positioned within the distal flange 26 to provide structural support to the retractor 18 within a patient's body. The proximal and distal O-rings can be substantially flexible or substantially rigid as needed, same or different from one another, for use in a particular application.

As shown in this embodiment, the device 10 can include one or more stability threads in the form of one or more rings disposed around a perimeter of the retractor 18, e.g., three rings 32 longitudinally spaced equidistantly or any other distance apart and extending around a perimeter of the inner elongate portion 28 of the retractor 18. Generally, the rings 32 can be disposed around a perimeter of the retractor 18 in at least the inner elongate portion 28 of the retractor 18 to help provide structural integrity to the retractor 18.

The rings 32 can have any size, shape, and configuration, same or different from any of the other rings 32. The rings 32 can have a size and shape corresponding to a portion of the retractor 18 to which they are respectively mated. The retractor 18 in this illustrated embodiment has a generally circular cross-sectional shape in at least the inner elongate portion 28 thereof, so the rings 32 can have a similar substantially circular shape and be disposed around a circumference of the inner elongate portion 28 such that the rings 32 surround at least a portion of a passageway 34 extending through the retractor 18. As shown in this embodiment, the rings 32 can be disposed around a perimeter of the retractor 18 with each ring 32 being in a plane parallel to planes of the other rings 32 such that center points of each of the rings 32 can be axially aligned with each other and with a central longitudinal axis A of the device 10 at least when the device 10 is in a default, initial position as shown in FIGS. 1 and 2. The planes of the rings 32 can also be parallel to a proximal surface of the housing 12, e.g., the proximal surface 14a of the seal base 14, such that a surgical instrument inserted into the passageway 34 can extend at a non-zero angle to the planes of the rings 32.

The rings 32 can be disposed within a sidewall of the inner elongate portion 28, as shown, such that the rings 32 can be contained within the retractor 18 and not obstruct an inner surface 28I of the inner elongate portion 28, e.g., a surface at least partially defining the passageway 34 extending through the retractor 18, such that the rings 32 do not protrude into the passageway 34. Although, in some embodiments the rings 32 can be coupled to the inside surface 28I and/or an outside surface 28O of the inner elongate portion 28. A diameter 32D of the rings 32 can thus be substantially equal to the diameter (s) of the portion(s) of the retractor 18 to which the rings 32 are attached, although the diameter 32D of the rings 32 can slightly vary from the inner diameter 28D of the inner elongate portion 28D depending on where the rings 32 are mated to the inner elongate portion 28. In this illustrated embodiment, the inner elongate portion 28 has a substantially cylindrical shape with a substantially constant inner diameter 28D, and the rings 32 correspondingly have substantially equal diameters 32D that are slightly greater than the inner diameter 28D of the inner elongate portion 28 since the rings 32 are disposed within the inner elongate portion 28 such that they do not protrude into the inner elongate portion 28.

The rings 32 can be substantially flexible or substantially rigid as needed, same or different from one another, for use in a particular application. The rings 32 can be made from a material that is more rigid than a material used to form the retractor 18, which can help provide structural support to the retractor 18 and provide additional hoop strength in the portion of the retractor 18 including the rings 32, e.g., the inner elongate portion 28, to help dilate the tissue opening in which the device 10 is positioned and/or hold the opening at a substantially constant size and shape once the device 10 is positioned within the opening.

With the rings 32 disposed around a perimeter of the retractor 18 and longitudinally spaced a non-zero distance apart as illustrated in this embodiment, the rings 32 can form ridges 36 on an outside surface of the retractor 18, e.g., on the outside surface 28O of the inner elongate portion 28. The ridges 36 can be generally configured to facilitate positioning of the device 10 in tissue by gripping the tissue, thereby helping to stabilize and prevent longitudinal movement of the device 10. The ridges 36 can also be configured to urge tissue in which the device 10 is positioned toward a shape of the rings 32, thereby helping to dilate or expand an opening in tissue to a size and shape more effective for passing surgical instruments therethrough.

Figure 3:
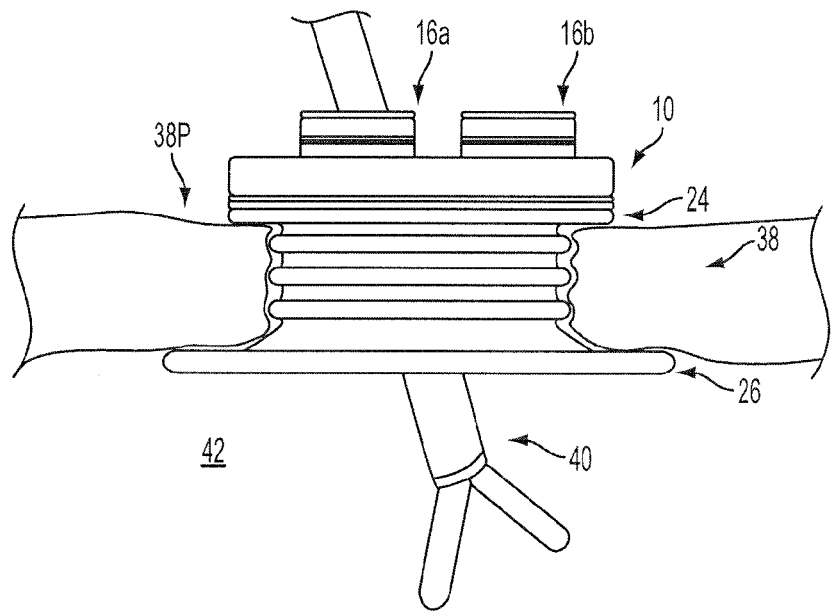
FIG. 3 is a side, partially cross-sectional view of the device of FIG. 1 positioned in tissue with a surgical instrument inserted through the device.

In use, as illustrated in FIG. 3, the device 10 can be positioned within a tissue 38 to provide access to a body cavity 42 underlying the tissue 38. The device 10 can be positioned within the tissue 38 in a variety of ways. In one embodiment, the device 10 can be positioned in tissue fully assembled in the default position shown in FIGS. 1 and 2. In another embodiment, the device 10 can be positioned partially assembled in the tissue 38 and be fully assembled with a portion of the device 10 positioned in the tissue 38, e.g., the retractor 18 can first be positioned in the tissue 38 and the housing 12 subsequently coupled thereto. If the tissue 38 and/or the retractor 18 are adequately flexible, the retractor 18 can be angled or pivoted to a desired position to ease attachment of the housing 12 to the retractor 18.

However positioned within the tissue 38, as illustrated in this embodiment, the retractor 18 as fully assembled can be positioned within an opening or incision formed in the tissue 38, e.g., in the umbilicus, with the proximal and distal flanges 24, 26 of the retractor 18 positioned on opposed sides of the tissue 38. The proximal flange 24 in the proximal portion of the retractor 18 can be positioned on one side of the tissue 38 with a distal surface of the proximal flange 24 positioned on and/or proximal to a proximal surface 38P of the tissue 38. The distal flange 26 of the retractor 18 can be positioned on and/or distal to a distal surface 38D of the tissue 38 in the body cavity 42. The inner elongate portion 28 of the retractor 18 can thereby be positioned within the tissue 38 with the working channel or passageway 34 of the retractor 18 extending through the tissue 38 to provide a path of access to the body cavity 42. As mentioned above and as shown in FIG. 3, the ridges 36 formed by the rings 32 can grip the tissue 38 within the opening and urge the opening to conform to the shape of the rings 32, e.g., substantially circular as shown.

With the surgical access device 10 assembled and positioned in the tissue, one or more surgical instruments can be inserted therethrough and into the body cavity 42 where the instruments can help perform any type of surgical procedure. One or more surgical instruments can be inserted through the device 10 and into the body cavity 42 through any of the sealing ports 16a, 16b, e.g., a pair of movable jaws 40 inserted through the first sealing port 16a, to help perform at least a portion of a surgical procedure. If the tissue 38 and/or the retractor 18 are adequately flexible, the retractor 18 can be angled or pivoted during use of the device 10 with the movable jaws 40 and/or other surgical tools inserted therethrough. Although a pair of movable jaws 40 are shown inserted through the device 10, any surgical device such as a grasper, a scoping device (e.g., an endoscope, a laparoscope, and a colonoscope), a cutting instrument, etc., can be inserted through the device 10. A person skilled in the art will appreciate that the term "grasper" as used herein is intended to encompass any surgical instrument that is configured to grab and/or attach to tissue and thereby manipulate the tissue, e.g., forceps, retractors, movable jaws, magnets, adhesives, stay sutures, etc. A person skilled in the art will also appreciate that the term "cutting instrument" as used herein is intended to encompass any surgical instrument that is configured to cut tissue, e.g., a scalpel, a harmonic scalpel, a blunt dissector, a cautery tool configured to cut tissue, scissors, an endoscopic linear cutter, a surgical stapler, etc.

At any point before, during, or after a surgical procedure, the housing 12 in full or part can be released from the retractor 18, and the retractor 18 can be removed from the tissue 38. With the housing 12 of the device 10 disengaged from the retractor 18, the passageway 34 of the retractor 18 can still provide access to the body cavity 42 underlying the tissue 38. One or more surgical instruments can be advanced through the passageway 34, such as a waste removal bag configured to hold waste material, e.g., dissected tissue, excess fluid, etc., from the body cavity 42. The bag can be introduced into the body cavity 42 through the retractor's passageway 34 or other access port. A person skilled in the art will appreciate that one or more surgical instruments can be advanced through the retractor's passageway 34 before and/or after the housing 12 has been attached to the retractor 18.

Figure 4:
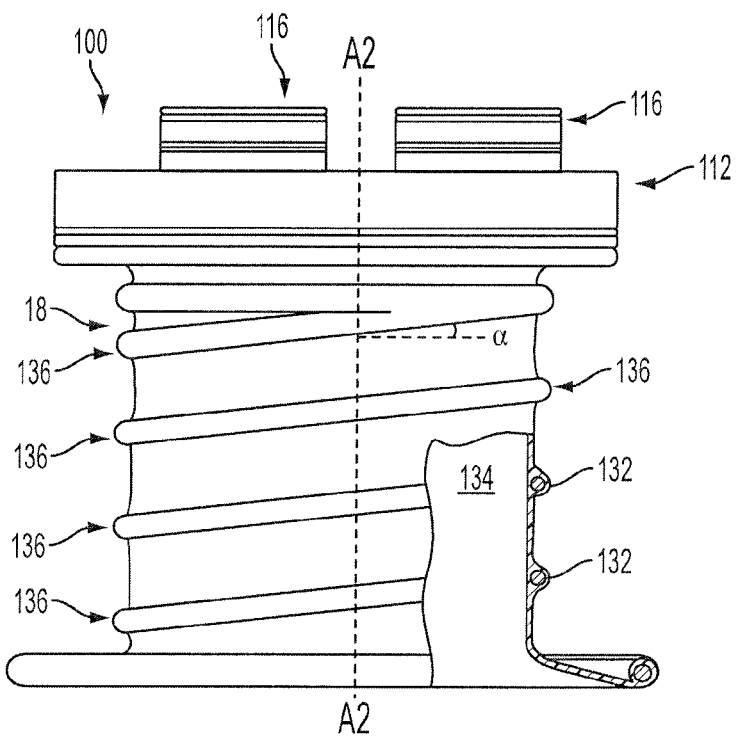
FIG. 4 is a side, partially cross-sectional view of one embodiment of a surgical access device having a plurality of angled rings disposed around a retractor of the device.
Figure 5:
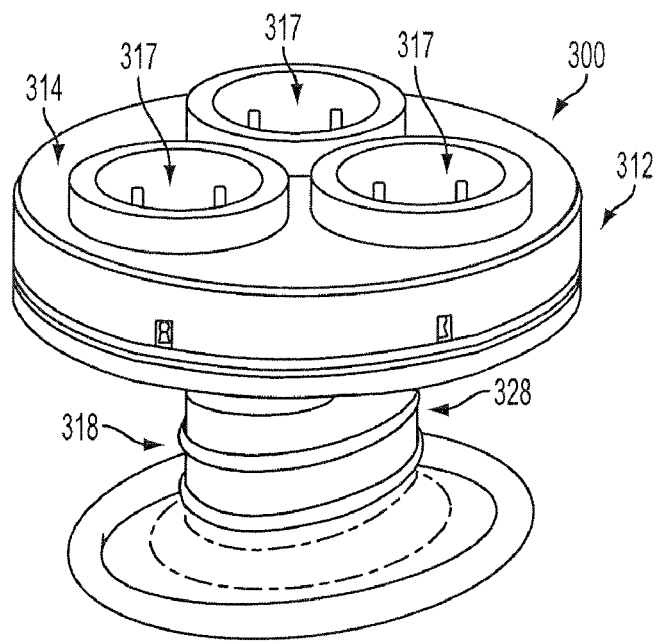
FIG. 5 is a perspective view of one embodiment of a surgical access device having a retractor with an elliptical cross-sectional shape.
Figure 6:
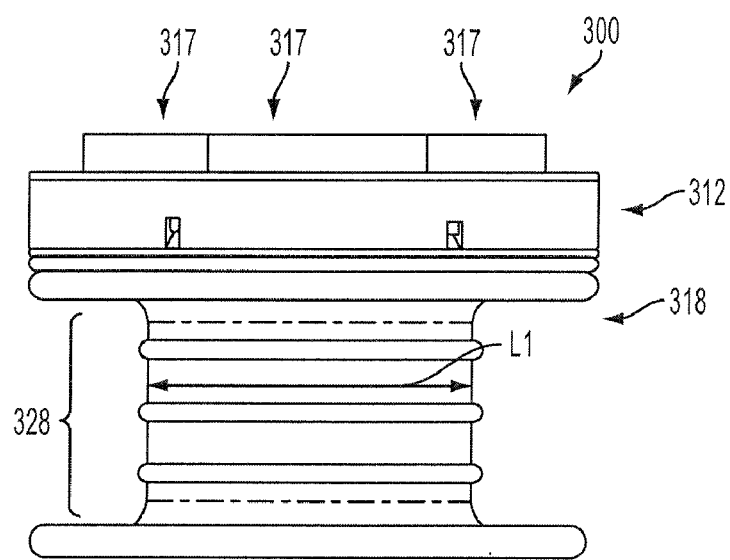
FIG. 6 is a side view of the device of FIG. 5 showing a major axis length of the retractor.
Figure 7:
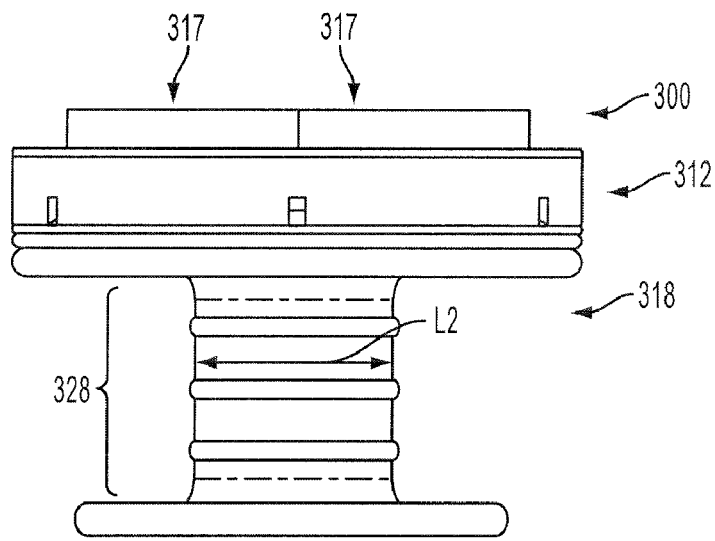
FIG. 7 is a side view of the device of FIG. 5 showing a minor axis length of the retractor.
Figure 8:
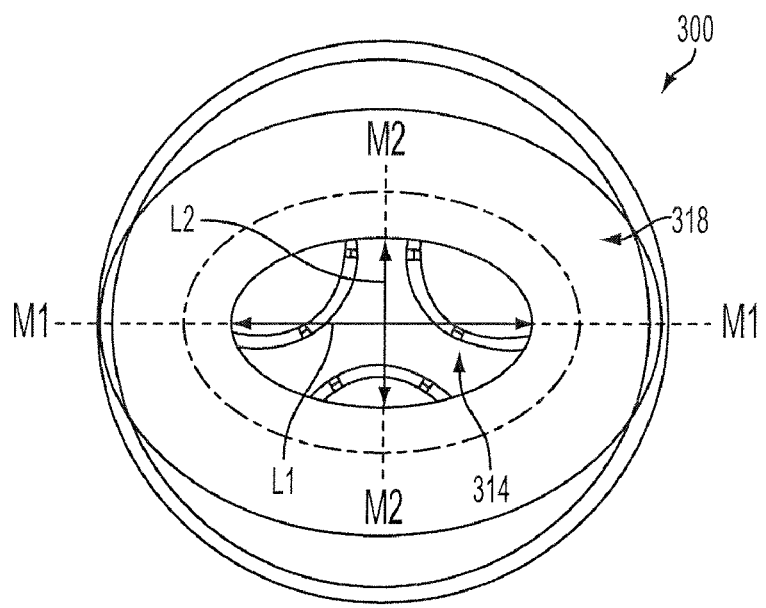
FIG. 8 is a distal end view of the device of FIG. 5.

FIG. 4 illustrates another embodiment of a surgical access device 100 that includes at least one stability thread in the form of at least one ring 132 configured to form at least one ridge 136 on an outer surface thereof. The surgical access device 100 can be configured and used similar to the surgical access device 10 discussed above and can include a housing 112, similar to the housing 12 discussed above, that is configured to seat one or more sealing ports 116 therein. The housing 112 can also be configured to be releasably or fixedly mated to a retractor 118. The retractor 118 and the rings 132 can be similar to the retractor 18 and the rings 32 discussed above, but unlike in the device 10 above, in this embodiment the rings 132 mated to the retractor 118 are angled relative to a passageway 134 extending through the retractor 118. In other words, planes of each of the rings 132 can be parallel with each other but can be at any angle α between 0° and +/−90° relative to a central longitudinal axis A2 of the device 100 at least when the device is in a default, initial position as shown in FIG. 4. The angle α can be substantially equal for each of the rings 132 as shown, or the angle α can vary between one or more rings 132. The rings 132 being angled can help retain the device 100 within tissue by increasing the device's resistance to longitudinal movement relative to the tissue. The angled rings 132 can be configured as discrete, independent members as shown in this embodiment, or the angled rings 132 can be configured as a continuous thread that spirals around at least a portion of a perimeter of the retractor 118 in a helical pattern.

FIGS. 5-8 illustrate yet another embodiment of a surgical access device 300 that includes at least one stability thread in the form of at least one ring (obscured from view in FIGS. 5-8) configured to form at least one ridge 336 on an outer surface thereof. The surgical access device 300 can be configured and used similar to the surgical access devices 10, 100 discussed above and can include a housing 312, similar to the housing 12 discussed above, that is configured to seat one or more sealing ports therein, e.g., three sealing ports (not shown) seated in three sealing port openings 317 formed in a seal base 314 of the housing 312. The housing 312 can also be configured to be releasably or fixedly mated to a retractor 318. The retractor 318 and the rings can be similar to the retractors 18, 118 and the rings 32, 132 discussed above, but unlike in the devices 10, 100 above, in this embodiment, the retractor 318 can have a non-circular cross-sectional shape in the form of an ellipse having a major axis M1 and a minor axis M2. A working channel or passageway 334 extending through the retractor 318 can thus also have an elliptical shape, with the rings and hence also the ridges 336 having an elliptical shape. Although the rings, and thus the ridges 336, are shown in this embodiment as continuously spiraling around an inner elongate portion 328 of the retractor 318, as discussed above the rings and the ridges 336 can disposed around any portion of the retractor 318 and/or be configured as discrete members. In an exemplary embodiment, the retractor 318 can be substantially flexible to allow at least the inner elongate portion 328 of the retractor 318 to deform when the device 300 is positioned in tissue, as discussed further below. The housing 312 attached to the retractor 318 can have any shape, e.g., substantially circular as shown.

Major and minor widths L1, L2 of the passageway 334 respectively along the major and minor axes M1, M2 of the retractor 318 can have any length. In an exemplary embodiment, the minor axis width L2 can be about 15 mm and the major axis width L1 can be about 25 mm, which can allow the retractor 318 to be positioned within a tissue opening having a longitudinal length of about 1 in. (25.4 mm).

Figure 9:
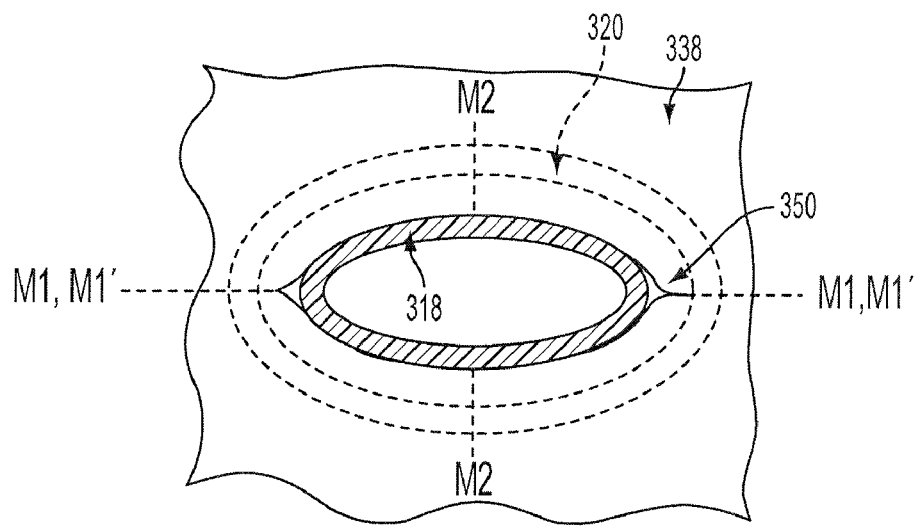
FIG. 9 is a distal end view of the device of FIG. 5 positioned in an opening in tissue with a major axis of the retractor being substantially parallel to a major axis of the opening.

In use, as shown in FIG. 9, the retractor 318 can be positioned within an opening 350 formed in tissue 338 similar to that discussed above for the device 10 with the retractor 318 in a first position with the major axis M1 of the retractor 318 being substantially parallel to a major axis M1' of the opening 350. Because openings formed in tissue can often have a linear shape, e.g., as a man-made linear cut in tissue, it can be easier to position an elliptical retractor having a minor axis length that is less than a major axis length within the opening than a circular retractor having substantially equal minor and major axis lengths. With the retractor 318 positioned in the tissue 350 in the first position, the opening 350 can conform to the shape of the retractor 318, e.g., be expanded or deformed from a linear shape to an elliptical shape having major and minor axis lengths substantially equal to the major and minor axis widths L1, L2 of the retractor 318.

Figure 10:
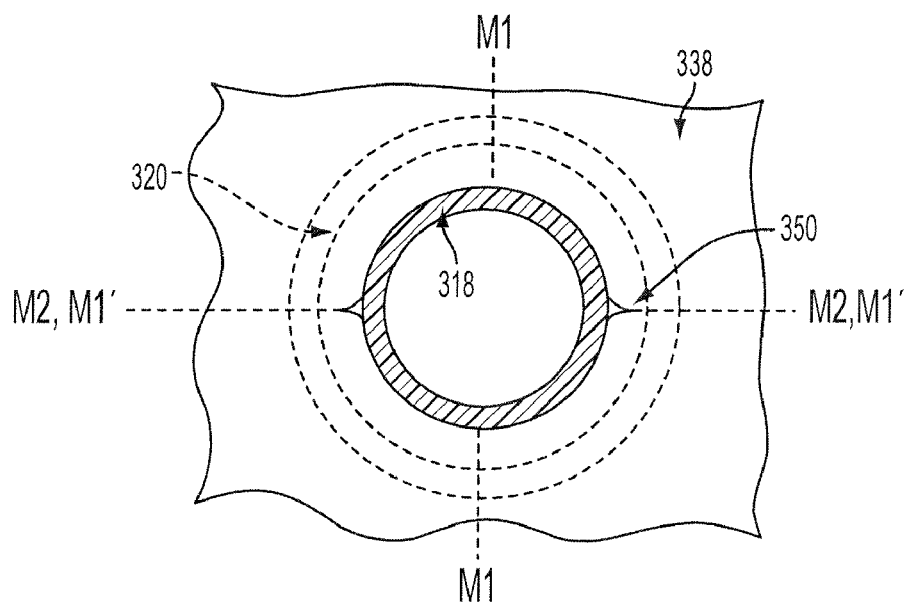
FIG. 10 is a distal end view of the device of FIG. 5 rotated from its position in the tissue of FIG. 9 with a minor axis of the retractor being substantially parallel to the major axis of the opening in tissue.

The retractor 318 can be rotated any amount clockwise and/or counterclockwise within the tissue 338, e.g., by holding and rotating the proximal retractor base 320 outside the body, to move the retractor 318 to a second position in which the major axis M1 of the retractor 318 can be at a non-zero angle to the major axis M1' of the opening 350 such that the major axes M1, M1' are no longer substantially parallel. As shown in one embodiment in FIG. 10, the retractor 318 can be rotated about +/−90° within the opening 350 such that the major axis M1 of the retractor 318 can be substantially perpendicular to the major axis M1' of the opening 350 and the minor axis M2 of the retractor M2 can be substantially parallel to the major axis M1' of the opening 350. Moving the retractor 318 from the first position to the second position can further expand or deform the shape of the opening 350. The retractor 318 in the second opening can attempt to urge the opening 350 to an elliptical shape, but compressive forces exerted by the tissue 338 on the retractor 318 can exceed the forces exerted by the retractor 318 on the tissue 338. The rings of the device 300 can help counteract the compressive forces exerted on the retractor 318 by the tissue and therefore, as illustrated in FIG. 10, the retractor 318, including the rings and the ridges 336 positioned within the tissue 338, can expand or deform to have a substantially circular cross-sectional shape in the second position. The opening 350, generally conforming to the shape of the retractor 318, can thus also have a substantially circular shape, which can help maximize an amount of available working space through the tissue 338 relative to a linear or elliptical opening.

Although the retractor 318 is shown in FIGS. 9 and 10 positioned in the tissue 338 and rotated relative thereto without the housing 312 attached to the retractor 318, the housing 312 can optionally be attached to the retractor 318 when the retractor 318 is positioned within the tissue 338 and/or rotated relative to the tissue 338.

In another embodiment of a surgical access device, a stability thread disposed around a perimeter of a retractor of the device can be configured to be mechanically adjustable such that a cross-sectional size and/or shape of the retractor can be selectively changed. In this way, the device can be selectively expanded, e.g., increase a diameter of a retractor of the device, and contracted, e.g., decrease the diameter of the retractor. The mechanically adjustable stability thread can be configured to be adjusted from outside a body of a patient when the device is positioned in the patient's tissue. The cross-sectional size and/or shape of tissue in which the device is positioned can thus also be mechanically adjusted generally in proportion to the mechanical adjustment of the device. Expansion of the retractor can allow the device to retract the tissue and provide for a larger access opening through the tissue, while contraction of the retractor can allow for easier initial positioning of the retractor within the tissue and easier removal of the retractor therefrom.

Figure 11:
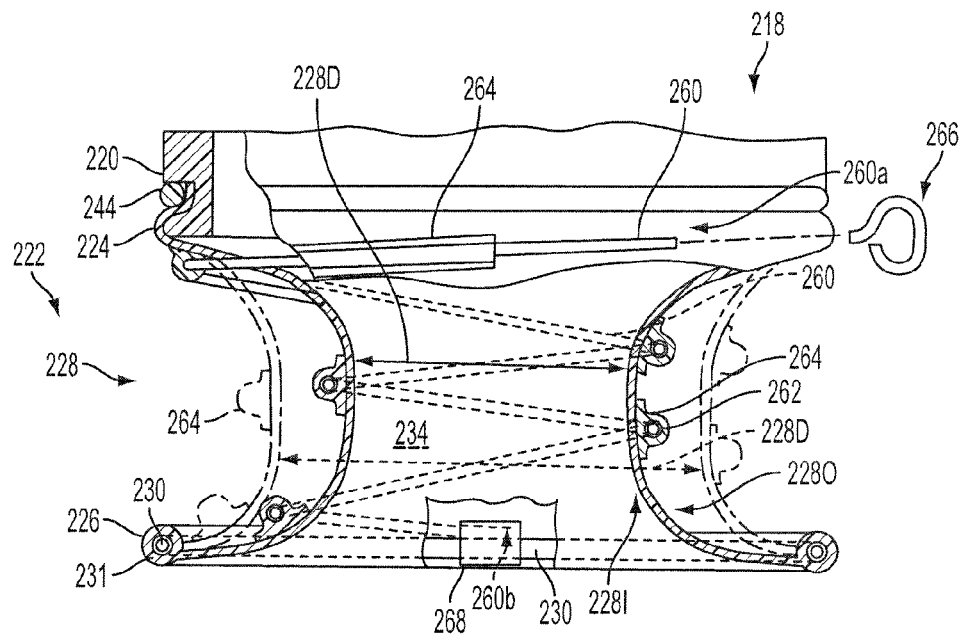
FIG. 11 is a side, partially cross-sectional view of one embodiment of a retractor of a surgical access device having a mechanically adjustable diameter.

In one embodiment of a surgical access device having a mechanically adjustable retractor diameter, illustrated in FIG. 11, the device can be configured and used similar to the surgical access devices 10, 100, 300 discussed above and can include a housing (not shown), similar to the housings 12, 112, 312 discussed above, that is configured to seat one or more sealing ports therein and configured to be releasably or fixedly mated to a retractor 218. The retractor 218 can be similar to the retractors 18, 118, 318 discussed above, have a circular, elliptical, or other cross-sectional shape, and include a proximal retractor base 220 coupled to a substantially flexible distal portion 222 having a proximal flange 224 and a distal flange 226 with an inner elongate portion 228 extending therebetween. As discussed above regarding the device 10 of FIGS. 1 and 2, a retractor retaining band 244 can be positioned between the proximal retractor base 220 and the flexible distal portion 222 to help form a secure seal therebetween.

A distal o-ring 230 can optionally be positioned within a sheath 231 positioned in the distal flange 226 to provide structural support to the retractor 218 within a patient's body. The distal o-ring 230 can be substantially rigid, e.g., a metal wire, as shown in the embodiment illustrated in FIG. 11, to allow the distal flange 226 to have a substantially fixed diameter. In other words, the distal flange 226 of the retractor 218 can be unaffected by adjustment of the retractor's diameter. With the distal flange 226 having a substantially fixed diameter, the retractor 218 can be configured to more effectively grip a distal surface of tissue in which the retractor 218 is positioned, thereby helping to maintain the retractor 218 in a more stable position when positioned in tissue.

Unlike in the devices 10, 100, 300 above, in this embodiment the retractor 218 can include an adjustable stability thread in the form of an actuation member 260 disposed around a perimeter of a retractor 218. Generally, the actuation member 260 can be configured to selectively effect a change in a diameter of the retractor 218 such that the retractor 218 changes in cross-sectional shape and/or size.

The actuation member 260 can have a variety of shapes, sizes, and configurations. The actuation member 260 can have a circular cross-sectional shape as shown to help facilitate smooth movement of the actuation member 260 around the perimeter of the retractor 218, although the actuation member 260 can have any cross-sectional shape. The actuation member 260 can also have any longitudinal length configured to allow the actuation member 260 to helically wind around a perimeter of the retractor 218 as discussed further below. As will be appreciated by a person skilled in the art, the actuation member 260 can be formed from any one or more materials, e.g., braided spring steel, a shape memory material such as Nitinol, etc., with the actuation member 260 in an exemplary embodiment being a flexible and biocompatible cable.

Similar to the rings 32, 132, 332 discussed above, the actuation member 260 as illustrated in this embodiment can be configured as a continuous thread that extends along and around, e.g., in a spiral configuration, at least a portion of the perimeter of the retractor 218 in a helical pattern. In an exemplary embodiment, the actuation member 260 can spiral around an entire longitudinal length of the retractor's inner elongate portion 228 to allow adjustment of a diameter 228D of the inner elongate portion 228, which can correspond to a diameter of an inner pathway or working channel 234 extending through the retractor 218. The actuation member 260 can loop any number of times, including less than one time, around the perimeter of the retractor 218, e.g., at least two loops as shown in FIG. 11, with the loops longitudinally spaced equidistantly or any other distance apart and extending around the perimeter of the retractor 218.

The actuation member 260 can be coupled to the retractor 218 in a variety of ways. Similar to the rings 32, 132, 332 discussed above, the actuation member 260 can be coupled to an inside surface 228I of the inner elongate portion 228, an outside surface 228O of the inner elongate portion 228, and/or be disposed within a sidewall of the inner elongate portion 228. In an exemplary embodiment, as shown in FIG. 11, the actuation member 260 can be coupled to the outside surface 228O of the inner elongate portion 228 by extending through an inner lumen 262 extending around the outside surface 228O. The inner lumen 262 can be integrally formed with the retractor 218, e.g., formed within the sidewall of the inner elongate portion 228, or as shown in this embodiment the inner lumen 262 can be formed in a lumen sheath 264 attached to the outside surface 228O of the inner elongate portion 228. The lumen sheath 264 extending around the perimeter of the inner elongate portion 228 can thereby form at least one ridge on the outside surface 228O thereof that can be configured similar to the ridges 36, 136, 336 discussed above. The longitudinal length of the actuation member 260 can extend through the inner lumen 262, and first and second terminal ends 260a, 260b of the actuation member 260 can be respectively coupled to an actuator 266 in a proximal portion of the retractor 218 and to a coupling mechanism 268 in a distal portion of the retractor 218. Although the actuator 266 is attached to the retractor 218 in this embodiment, the actuator 266 can be attached to any portion of a housing configured to be coupled to the retractor 218. Further, in some embodiments the actuator 266 can be positioned at a distal portion of the retractor 218 with the actuation member's second terminal end 260b attached to the actuator 266 and the actuation member's first terminal end 260a attached to a proximal portion of the retractor 218 or in any portion of a housing configured to be attached to the retractor 218.

The actuator 266 coupled to the first terminal end 260a of the actuation member 260 can have a variety of shapes, size, and configurations. Generally, the actuator 266 can be configured to be at least partially positioned and manipulated outside a body of a patient in which the retractor 218 is positioned to effect movement of the actuation member 260 to adjust the diameter 228D of the retractor's inner elongate portion 228. As illustrated in FIG. 11, the actuator 266 can include a handle positioned outside the retractor 218. The handle can include a finger loop, as shown in FIG. 11, although as will be appreciated by a person skilled in the art the handle can have a variety of shapes, sizes, and configurations, e.g., a knob, a T-bar, etc. The handle can be configured to be movable relative to the retractor 218 to actuate the actuation member 260.

The coupling mechanism 268 coupled to the second terminal end 260b of the actuation member 260 can also have a variety of shapes, size, and configurations. Generally, the coupling mechanism 268 can be configured to secure the actuation member 260 to an opposite end of the retractor 218 from where the actuator 260 is positioned to allow the actuation member 260 to extend along at least a partial longitudinal length of the retractor's inner elongate portion 228. As shown in this illustrated embodiment, the coupling mechanism 268 can include a block fixedly coupled to the distal o-ring 230. The block can have any shape, e.g., rectangular as shown. In some embodiments, the actuation member 260 can be directly coupled to the distal o-ring 230 or to a sheath 231 encasing the distal o-ring 230 within the distal flange 226.

In use, the retractor 218 can be positioned within an opening formed in tissue similar to that discussed above for the device 10. Before and/or after the retractor 218 is positioned in tissue, the actuator 266 can be moved in a first direction, e.g., in a direction away from the retractor 218, to pull the actuation member 260 to increase tension of the actuation member 260 and constrict the diameter 228D of the inner elongate portion 228 such that the retractor 218 can be in an constricted state, shown by the solid lines of the inner elongate portion 228 in FIG. 11. With the actuation member 260 fixedly coupled to the coupling mechanism 268, adequate tension of the actuation member 260 can be provided to allow the actuation member 260 can slide through the inner lumen 262 and change the diameter 228D of the inner elongate portion 228. The actuator 266 can be moved in a second direction opposite to the first direction, e.g., in a direction toward the retractor 218, to reduce a tension of the actuation member 260 to loosen the actuation member 260 and expand the diameter 228D of the inner elongate portion 228 such that the retractor 218 can be in an expanded state, shown by the broken lines of the inner elongate portion 228 in FIG. 11. As shown in FIG. 11, the retractor 218 can be configured such that effecting a change in the diameter 228D of the retractor 218, does not substantially change a longitudinal length of the retractor 218, which can help keep the retractor 218 in secure engagement with proximal and distal surfaces of the tissue in which the retractor 218 is positioned.

Although the retractor 218 can be configured in any state as a default, the retractor 218 in this illustrated embodiment is configured to be in the expanded state as a default. In this way, the actuation member 260 can be tightened for positioning the retractor 218 within tissue, e.g., by pulling the handle, to move the retractor 218 to the second state in which it has a smaller diameter. Once the retractor 218 is positioned within an opening in tissue, e.g., with the proximal and distal flanges 224, 226 positioned on opposite sides of the tissue, the actuation member 260 can be loosened, e.g., by releasing the handle, to allow the retractor 218 to move toward the first state. The retractor 218 can thus dynamically adjust to the size of the opening and dilate the opening by exerting an outward force upon the tissue. Depending on the elasticity of the tissue in which the retractor 218 is positioned, the retractor 218 can move fully or partially to its default state when the handle has been released. To remove the retractor 218 from the tissue, the actuator 262 can be actuated, e.g., the handle can be pulled, to reduce the inner elongate portion's diameter 228D, which can make the retractor 218 easier to move through and out of the tissue opening.

Figure 12:
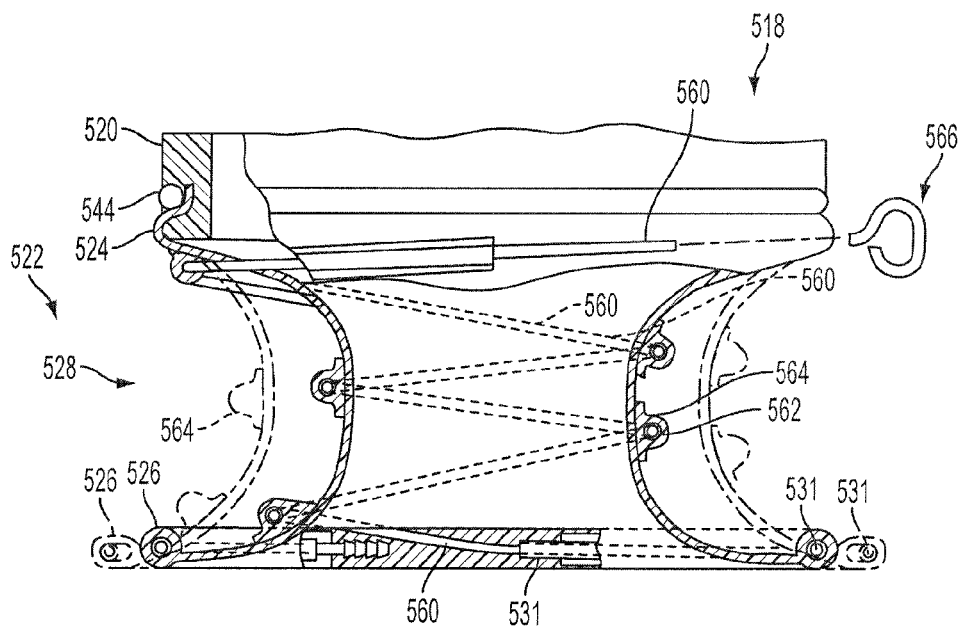
FIG. 12 is a side, partially cross-sectional view of another embodiment of a retractor of a surgical access device having a mechanically adjustable diameter.

In another embodiment of a surgical access device having a mechanically adjustable retractor diameter, shown in FIG. 12, the device can be configured and used similar to the surgical access devices discussed above and can include a housing (not shown), similar to the housings discussed above, that is configured to seat one or more sealing ports therein and configured to be releasably or fixedly mated to a retractor 518. The retractor 518 can be similar to the retractors 18, 118, 218, 318 discussed above, have a circular, elliptical, or other cross-sectional shape, and include a proximal retractor base 520 coupled to a substantially flexible distal portion 522 having a proximal flange 524 and a distal flange 526 with an inner elongate portion 528 extending therebetween. As discussed above regarding the device 10 of FIGS. 1 and 2, a retractor retaining band 544 can be positioned between the proximal retractor base 520 and the flexible distal portion 522 to help form a secure seal therebetween. The device can also include an adjustable stability thread in the form of an actuation member 560 disposed around a perimeter of a retractor 518.

The actuation member 560 can generally be configured and used similar to the actuation member 260 of FIG. 11 and be actuated using an actuator 566 similar to the actuator 266 discussed above. However, the actuation member 560 in this illustrated embodiment can be configured to adjust a diameter of the retractor's distal flange 526 in addition to the retractor's inner elongate portion 528. As shown, an inner lumen of the retractor 518 in which the actuation member 560 extends can extend through a lumen sheath 564 attached to the inner elongate portion 228 and through a sheath 531 positioned in the distal flange 526. In this way, the actuation member 560 can be configured to move through the inner lumen and selectively effect a change in a diameter of the retractor 518 in the inner elongate portion 528 and in the distal flange 526 such that the retractor 518 can move between a first, expanded state, shown by the broken lines of the inner elongate portion 528 and the distal flange 526 in FIG. 12 and a second, constricted state, shown by the solid lines of the inner elongate portion 528 and the distal flange 526. Having a selectively adjustable distal flange can further facilitate positioning of the retractor 518 within tissue and removing the retractor 518 therefrom. Similar to the lumen sheath 264 discussed above, the lumen sheath 564 extending around the perimeter of the inner elongate portion 528 can form at least one ridge on an outside surface of the inner elongate portion 528.

A surgical access device having a mechanically adjustable stability thread disposed around a perimeter of a retractor of the device can optionally include a locking mechanism configured to hold the retractor in a fixed state with a fixed diameter. The locking mechanism can have a variety of shapes, sizes, and configurations. In one embodiment of a surgical device having a retractor and actuation member similar to the retractor 218 and the actuation member 260 of FIG. 11, the actuator can include a handle similar to the actuator 262 that instead of being configured as freely slidable to freely slide the actuation member, can be configured to be lockable, e.g., as a threaded handle configured to engage corresponding threads on the retractor 218 and be rotated to adjust tension of the actuation member attached thereto.

In another embodiment of a surgical access device 600 having an adjustable and lockable retractor diameter, shown in FIGS. 13-16, the device 600 can be configured and used similar to the surgical access devices discussed above and can include a housing 612, similar to the housings discussed above, that is configured to seat one or more sealing ports 616 therein and to fixedly mate to a retractor 618, although in some embodiments a housing of a device having an adjustable and lockable retractor diameter can be configured to be removably mated to a retractor. The retractor 618 can be similar to the retractors discussed above, have a circular, elliptical, or other cross-sectional shape, and include a substantially flexible distal portion having a distal flange 626 with an inner elongate portion 628 proximally extending therefrom. The device can also include an adjustable stability thread in the form of an actuation member 660 disposed around a perimeter of a retractor 618.

The housing 612 in this illustrated embodiment includes a seal base 614 that supports at least one sealing or access port 616 in one or more sealing port openings 617 formed therein, similar to the seal base 14 and the sealing ports 16a, 16b of FIGS. 1 and 2. The housing 612 also includes a ratchet ring 619 configured to couple to the actuation member 660, an inner ring 615 configured to mate the ratchet ring 619 to the seal base 614, and proximal and distal retractor couplers 621, 623 configured to engage and seat the retractor 618 therebetween and to mate with the seal base 614.

The actuation member 660 can generally be configured and used similar to the actuation members 260, 560 discussed above and be actuated using an actuator 666 similar to the actuators 266, 566 discussed above. The actuator 666 in this illustrated embodiment can be configured to adjust a diameter of the retractor's distal flange 626 in addition to the retractor's inner elongate portion 628 and can also be configured as a locking mechanism as discussed further below to hold the retractor 618 in a fixed state with a fixed diameter. As shown, an inner lumen of the retractor 618 in which the actuation member 660 extends can extend through a lumen sheath 664 attached to the inner elongate portion 628 and through a sheath 631 positioned in the distal flange 626. In this way, the actuation member 660 can be configured to move through the inner lumen and selectively effect a change in a diameter of the retractor 618 in the inner elongate portion 628 and in the distal flange 626 such that the retractor 618 can move between a first, expanded state, shown by the broken lines of the inner elongate portion 628 and the distal flange 626 in FIG. 13 and a second, constricted state, shown by the solid lines of the inner elongate portion 628 and the distal flange 626. Similar to the lumen sheaths 264, 564 discussed above, the lumen sheath 664 extending around the perimeter of the inner elongate portion 628 can form at least one ridge on an outside surface of the inner elongate portion 628.

Figure 13:
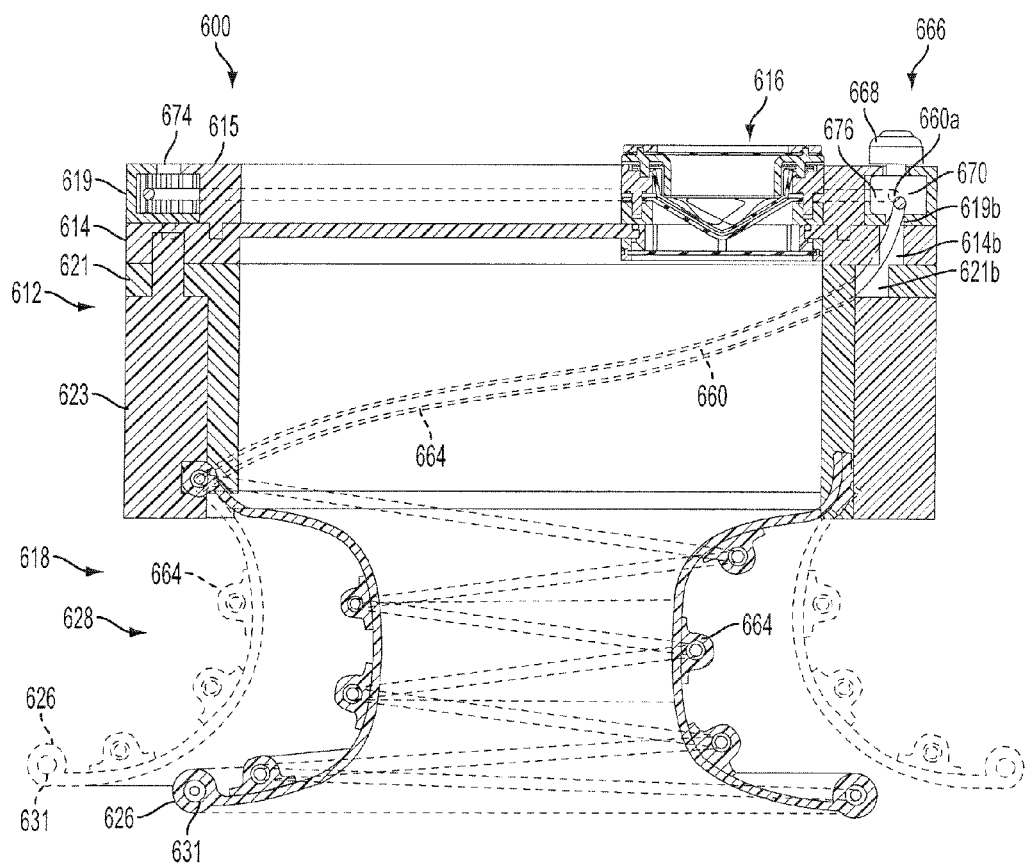
FIG. 13 is a side cross-sectional view of one embodiment of a surgical access device having a mechanically adjustable and lockable diameter.
Figure 14:
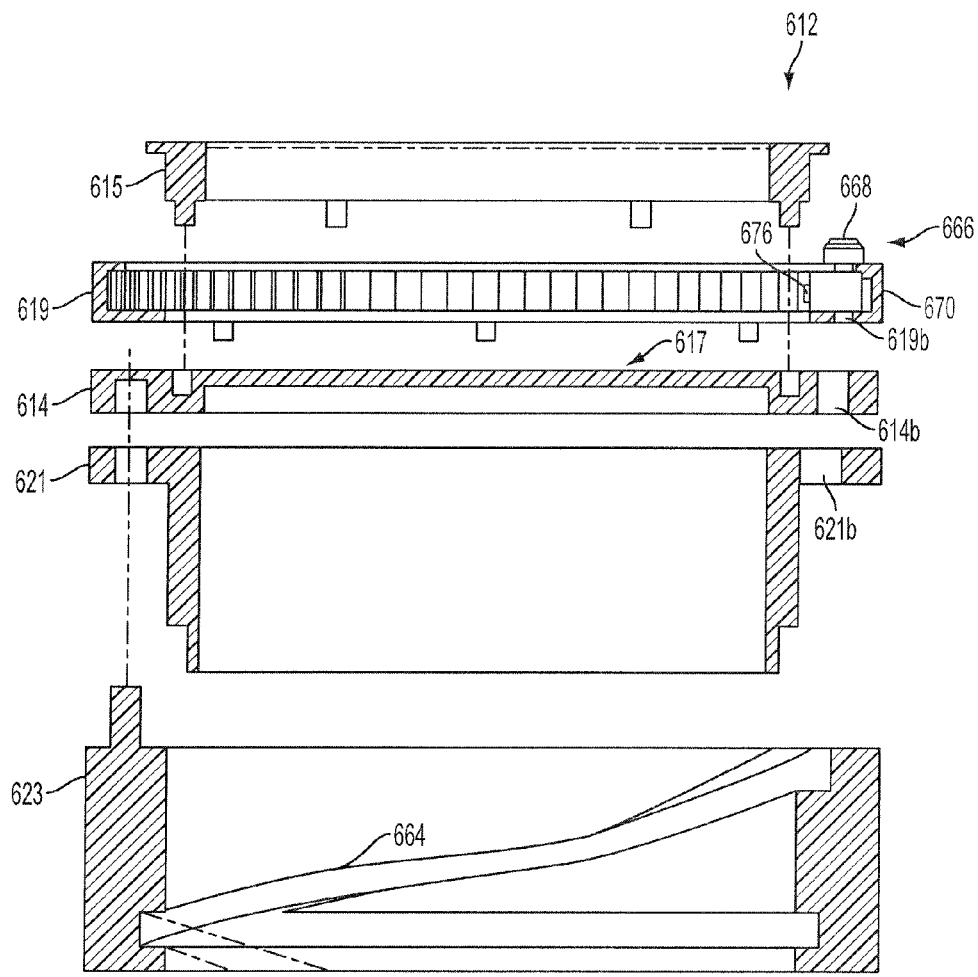
FIG. 14 is an exploded cross-sectional view of a housing of the device of FIG. 13.
Figure 15:
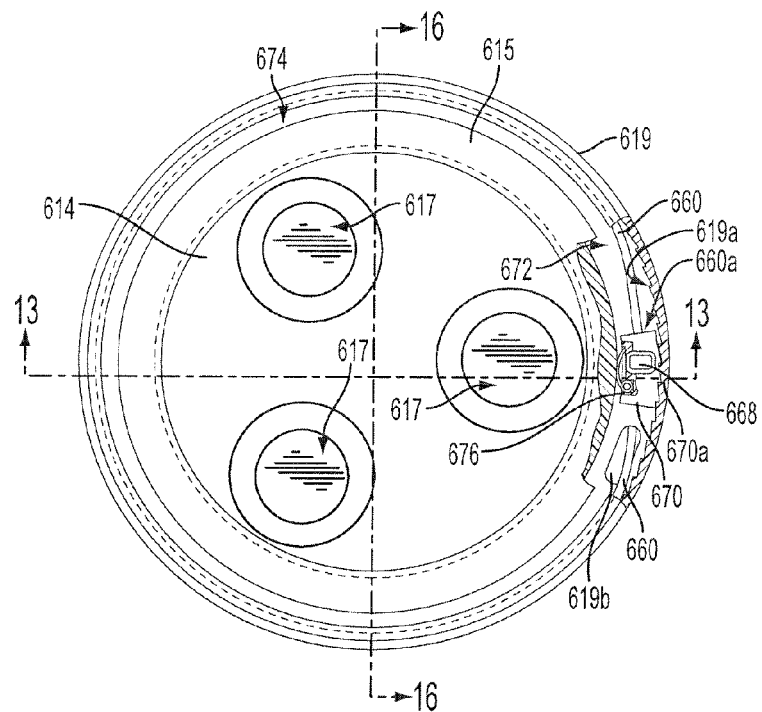
FIG. 15 is a partially cross-sectional, proximal end view of the device of FIG. 13.
Figure 16:
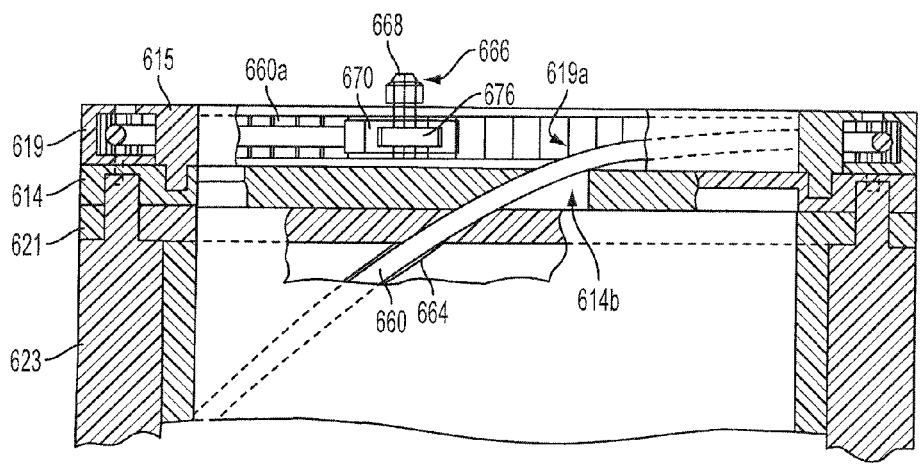
FIG. 16 is a side, partially cross-sectional view of the housing of the device of FIG. 13.

The actuator 666 can have a variety of shapes, size, and configurations. As shown in this embodiment, the actuator 666 can be configured as a ratchet mechanism configured to actuate the actuation member 660. The actuator 666 can include a pawl 670, as illustrated in FIGS. 13 and 15, configured to be at least partially disposed in a channel 672 formed in the ratchet ring 618 and be slidably movable therein. A knob 668 can be fixedly or removably attached to the pawl 670, although as will be appreciated by a person skilled in the art the knob 668 can have a variety of shapes, sizes, and configurations, e.g., a finger loop, a T-bar, etc. The knob 668 can extend from the pawl 670 disposed in the channel 672 and extend through a slide slot 674 defined by proximal surfaces of the inner ring 615 and the ratchet ring 619, thereby allowing the pawl 670 to be manipulated via the knob 668 from outside the housing 612. Although the knob 668 proximally extends from the pawl 670 in this embodiment, the knob 668 can extend from the pawl 670 in any direction, e.g., radially outward through a sidewall of the housing 612. The slide slot 674 can extend any distance around a circumference of the device 600, e.g., about 345° therearound as illustrated in FIG. 15. Although the actuator 666 is attached to the housing 612 in this embodiment, the actuator 666 can be attached to any portion of the housing 612. Further, in some embodiments the actuator 666 can be attached to the retractor, e.g., a proximal retractor base, of a surgical access device rather than the housing of the device, which can more easily allow for the housing to be removably coupled to the retractor.

The pawl 670 can include teeth 670a configured to engage corresponding teeth 619a formed around at least a portion of a circumference of the ratchet ring 619 of the housing 612. The pawl 670 is shown in this embodiment with three teeth 670a configured to engaged three housing teeth 619a at a time, but the pawl 670 can include any number of teeth 670a configured to engage any number of housing teeth 619a. The actuator 666 can also include a lock spring 676 coupled to the pawl 670 on a side of the pawl 670 opposite a side of the pawl 670 on which the teeth 670a are formed. The lock spring 676 can be configured to provide a bias force between a wall of the channel 672 and the pawl 670 to force the pawl 670 toward the housing's teeth 619a to keep the pawl 670 in a locked, fixed position relative to the housing 612 and the retractor 618 until the actuator 666 is actuated as discussed further below. Although the channel 672 engaged by the pawl 670 and the teeth 619a configured to be engaged by the pawl's teeth 670a are formed in or on the ratchet ring 619 in this embodiment, the pawl 670 can slidably engage any portion of the housing 612 or the retractor 618, and teeth engaged by the pawl 670 can be formed on any portion of the housing 612 or the retractor 618. As will be appreciated by a person skilled in the art, the complementary teeth 670a, 619a can have any size and shape configured to correspondingly engage each other. The pawl's teeth 670a can be configured to be selectively movable relative to the housing's teeth 619a to selectively adjust tension of the actuation member 660 through movement of the knob 668.

The actuator 666 can attach to the actuation member 660 in any way, such as by a first terminal end 660a of the actuation member 660 being attached to the pawl 670. The knob 668 can be configured to be at least partially positioned and manipulated outside a body of a patient in which the device 600 is positioned, while the pawl 670 can be configured to be at least partially disposed within the device 600 and to couple with the actuation member 660 to adjust tension of the actuation member 660 in response to actuation, e.g., movement, pushing, pulling, etc., of the knob 668.

The actuation member 660 can extend distally from the actuator 666 and distally extend around the retractor 618 in a spiral or helical pattern, with one or more components of the housing 612 and/or the retractor 618 having openings or lumens formed therein or therethrough for accommodating the actuation member 660. As shown, the actuation member 660 can extend from the pawl 670, pass through openings 619b, 614b, 621b respectively formed in the ratchet ring 619, the seal base 614, and the proximal retractor coupler 621, and pass into the inner lumen of the lumen sheath 664 that can extend from the inner elongate portion 628 and into the proximal retractor coupler 621.

In use, the retractor 618 can be positioned within an opening formed in tissue similar to that discussed above for the device 10. The actuator 666 can be selectively, mechanically actuated to selectively increase and/or decrease a tension of the actuation member 660 and hence to selectively increase and/or decrease a diameter of the retractor 618 before and/or after the retractor 618 is positioned in tissue. The knob 668 can be pushed in a radially inward direction relative to the retractor 618 and/or the housing 612 to counteract the bias force provided by the lock spring 676 and move the teeth 670a of the pawl 670 out of engagement from the teeth 619a of the ratchet ring 619. With the complementary teeth 619a, 670a disengaged, the pawl 670 can be freely slidably movable any distance through the channel 672 in a clockwise and/or counterclockwise direction. Moving the knob 668 and hence the pawl 670 in a first direction, e.g., counterclockwise, can reduce tension of the actuation member 660, while moving the knob 668 and the pawl 670 in a second, opposite direction, e.g., clockwise, can increase tension of the actuation member 660. In other words, moving the pawl 670 in the first direction can move a length of the actuation member 660 from inside the channel 672 such that a longer length of the actuation member 660 can extend around a perimeter of the retractor 618, thereby allowing the inner elongate portion 628 to expand. Similarly, moving the pawl 670 in the second direction can move a length of the actuation member 660 into the channel 672 such that a shorter length of the actuation member 660 can extend around a perimeter of the retractor 618, thereby constricting the inner elongate portion 628. The knob 668 can be moved in a radially outward direction relative to the retractor 618 and/or the housing 612 to reengage the lock spring 676 and to reengage the complementary teeth 619a, 670a such that the pawl 670 is prevented from moving with the pawl 670 and the actuation member 660 attached thereto in a fixed position relative to the retractor 618 such that the diameter of the retractor 618 can be locked in a fixed state until the actuator 666 is subsequently actuated to increase and/or decrease a diameter of the retractor 618.

As will be appreciated by those skilled in the art, any and all of the embodiments disclosed herein can be interchangeable with one another as needed. For example, an exemplary surgical access device kit could include multiple housings and seal bases with one or more retractors. Each seal base and housing combination can have different movable sealing port configurations enabling various combinations of movable sealing port movement as needed in particular application. Various release mechanism known in the art can be used to releasably attach the various base members and housings to a retractor.

There are various features that can optionally be included with any and all of the surgical access device embodiments disclosed herein. For example, a component of the device, such as a seal base, housing, retractor, etc., can have one or more lights formed thereon or around a circumference thereof to enable better visualization when inserted within a patient. As will be appreciated, any wavelength of light can be used for various applications, whether visible or invisible. Any number of ports can also be included on and/or through the surgical access devices to enable the use of various surgical techniques and devices as needed in a particular procedure. For example, openings and ports can allow for the introduction of pressurized gases, vacuum systems, energy sources such as radiofrequency and ultrasound, irrigation, imaging, etc. As will be appreciated by those skilled in the art, any of these techniques and devices can be removably attachable to the surgical access device and can be exchanged and manipulated as needed.

The embodiments described herein can be used in any known and future surgical procedures and methods, as will be appreciated by those skilled in the art. For example, any of the embodiments described herein can be used in performing a sleeve gastrectomy and/or a gastroplasty, as described in U.S. application Ser. No. 12/242,765 entitled "Surgical Access Device" filed on Sep. 30, 2008; U.S. application Ser. No. 12/242,711 entitled "Surgical Access Device with Protective Element" filed on Sep. 30, 2008; U.S. application Ser. No. 12/242,721 entitled "Multiple Port Surgical Access Device" filed on Sep. 30, 2008; U.S. application Ser. No. 12/242,726 entitled "Variable Surgical Access Device" filed on Sep. 30, 2008; U.S. application Ser. No. 12/242,333 entitled "Methods and Devices for Performing Gastrectomies and Gastroplasties" filed on Sep. 30, 2008; U.S. application Ser. No. 12/242,353 entitled "Methods and Devices for Performing Gastrectomies and Gastroplasties" filed on Sep. 30, 2008; and U.S. application Ser. No. 12/242,381 entitled "Methods and Devices for Performing Gastroplasties Using a Multiple Port Access Device" filed on Sep. 30, 2008, all of which are hereby incorporated by reference in their entireties.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., a seal base, a housing, a proximal retractor base, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
   a proximal housing having one or more sealing ports extending therethrough, each sealing port having a sealing element configured to form a seal around an instrument inserted through the sealing port;
   a distal flexible retractor including a proximal flange, a distal flange, and an elongate portion extending between the proximal and distal flanges, the elongate portion being configured to be positioned in tissue of a body to form a pathway therethrough into a body cavity with the proximal and distal flanges positioned on opposed sides of the tissue; and
   an actuation member spiraling around a perimeter of the retractor, the actuation member being configured to selectively effect a change in a diameter of the retractor, wherein
   the retractor has a lumen extending through a sidewall thereof, the actuation member being disposed in the lumen, and
   the retractor has a working channel extending therethrough configured to define the pathway, the lumen spiraling around the working channel, and the actuation member is configured to move within the lumen relative to the retractor to effect the change in the diameter of the retractor.

2. The device of claim 1, wherein a first terminal end of the actuation member is attached to a distal end of the retractor and a second terminal end of the actuation member extends through the proximal housing.

3. The device of claim 1, further comprising an actuator configured to change a tension of the actuation member to selectively effect the change in the diameter of the retractor.

4. The device of claim 3, wherein the actuator comprises a ratchet mechanism including a pawl configured to engage at least one of a plurality of teeth, the pawl being movable to selectively effect the change in the diameter of the retractor.

5. The device of claim 4, wherein the pawl is configured to be freely slidably movable in a first direction to selectively effect the change in the diameter of the retractor and to be prevented from moving in a second, opposite direction.

6. The device of claim 5, wherein the pawl is configured to move radially inward relative to the retractor to disengage the pawl from engagement with the at least one of a plurality of teeth to allow the pawl to move in the first direction or the second direction to engage at least one other of the plurality of the teeth.

7. The device of claim 3, wherein the actuator comprises a handle positioned outside the retractor.

8. The device of claim 1, wherein selectively effecting the change in the diameter of the retractor does not substantially change a longitudinal length of the retractor.

9. The device of claim 1, wherein the retractor in a default state has a first diameter, and wherein actuating the actuation member with the retractor in the default state moves the retractor to a second state in which the retractor has a second diameter that is less than the first diameter.

10. The device of claim 1, wherein the retractor in a default state has a first diameter, and wherein actuating the actuation member with the retractor in the default state moves the retractor to a second state in which the retractor has a second diameter that is greater than the first diameter.

11. The device of claim 1, wherein the actuation member is configured to be locked in a fixed position relative to the retractor to maintain the diameter of the retractor at a selected size.

12. The device of claim 1, wherein the actuation member is configured to move to change a length of the actuation member spiraling around the perimeter of the retractor to effect the change in the diameter of the retractor.

13. The device of claim 1, wherein the elongate portion has at least one ridge spiraling around an outside surface thereof, the actuator being located within the ridge.

14. The device of claim 1, wherein the actuation member is configured to selectively effect the change in the diameter of the retractor without directly contacting the tissue when the elongate portion of the flexible retractor is positioned in the tissue to form the pathway.

15. A surgical access device, comprising:
   a proximal housing having one or more sealing ports extending therethrough, each sealing port having a sealing element configured to form a seal around an instrument inserted through the sealing port;
   a distal flexible retractor including a proximal flange, a distal flange, and an elongate portion extending between the proximal and distal flanges, the elongate portion being configured to be positioned in tissue of a body to form a pathway therethrough into a body cavity with the proximal and distal flanges positioned on opposed sides of the tissue; and
   an actuation member spiraling around a perimeter of the retractor, the actuation member being configured to selectively effect a change in a diameter of the retractor, wherein
   the elongate portion has at least one ridge spiraling around an outside surface thereof, the actuator being located within the ridge, and the actuation member is configured to move within the ridge to change a length of the actuation member positioned within the ridge to effect the change in the diameter of the retractor.

16. The device of claim 15, wherein the retractor has a lumen extending through a sidewall thereof, the actuation member being disposed in the lumen.

17. A surgical access device, comprising:
a proximal external portion;
a distal portion including a flexible retractor having a working channel extending therethrough, the retractor having a lumen spiraling around the working channel, and the retractor being configured to be positioned in tissue of a body such that the working channel forms a pathway through the tissue into a body cavity; and
an actuation member disposed in the lumen and spiraling around a perimeter of the retractor, the actuation member being configured to selectively effect a change in a diameter of the retractor, wherein the actuation member is configured to slide through the lumen relative to the retractor to effect the change in the diameter of the retractor.

18. A surgical access device, comprising:
a proximal external portion;
a distal portion including a flexible retractor having a working channel extending therethrough, the retractor having a lumen spiraling around the working channel, and the retractor being configured to be positioned in tissue of a body such that the working channel forms a pathway through the tissue into a body cavity; and
an actuation member disposed in the lumen and spiraling around a perimeter of the retractor, the actuation member being configured to selectively effect a change in a diameter of the retractor, wherein the actuation member is configured to slide within the lumen to change a length of the actuation member positioned within the lumen to effect the change in the diameter of the retractor.

* * * * *